US006680187B2

(12) United States Patent
Moeckel et al.

(10) Patent No.: US 6,680,187 B2
(45) Date of Patent: Jan. 20, 2004

(54) NUCLEOTIDE SEQUENCES CODING FOR THE PTSI PROTEIN

(75) Inventors: Bettina Moeckel, Duesseldorf (DE); Stephan Hans, Osnabrueck (DE); Natalie Schischka, Bielefeld (DE); Walter Pfefferle, Halle (Westf.) (DE)

(73) Assignee: Degussa AG, Duesseldorf (DE)

( * ) Notice: Subject to any disclaimer, the term of this patent is extended or adjusted under 35 U.S.C. 154(b) by 71 days.

(21) Appl. No.: 09/950,788

(22) Filed: Sep. 13, 2001

(65) Prior Publication Data

US 2002/0132323 A1 Sep. 19, 2002

(30) Foreign Application Priority Data

Sep. 13, 2000 (DE) ........................................ 100 45 496

(51) Int. Cl.[7] ............................ C12N 9/12; C12N 1/21; C12N 1/20; C12N 15/52; C07H 21/04

(52) U.S. Cl. ........................ 435/194; 435/6; 435/252.3; 435/252.32; 435/252.33; 435/320.1; 536/23.2; 536/23.7; 536/24.32

(58) Field of Search ......................... 435/6, 194, 252.3, 435/252.32, 252.33, 320.1; 536/23.2, 23.7, 24.32

(56) References Cited

FOREIGN PATENT DOCUMENTS

| EP | 1 029 919 | 8/2000 |
|---|---|---|
| EP | 1108790 A2 | 6/2001 |
| WO | WO 01/00583 | 1/2001 |
| WO | WO 01/00802 | 1/2001 |
| WO | WO 01/00845 | 1/2001 |
| WO | WO 01/00847 | 1/2001 |

OTHER PUBLICATIONS

Database Swall "Online", EBI, XP002185708, Acc. No. P45597, "Phosphotransferase System Enzyme I of Xanthomonas Campestris", Nov. 1, 1995.

J. Cremer, et al., Applied and Environmental Microbiology, XP 000616281, vol. 57, No. 6, pp. 1746–1752, "Control of the Lysine Biosynthesis Sequence in Corynebacterium Glutamicum as Analyzed by Overexpression of the Individual Corresponding Genes", Jun. 1, 1991.

*Primary Examiner*—Elizabeth Slobodyansky
(74) *Attorney, Agent, or Firm*—Oblon, Spivak, McClelland, Maier & Neustadt, P.C.

(57) ABSTRACT

The present invention provides nucleotide sequences from Coryneform bacteria which code for the PtsI protein and a process for the fermentative preparation of amino acids using bacteria in which the ptsI gene is enhanced.

36 Claims, 2 Drawing Sheets

Figure 1: Plasmid pEC-T18mob2
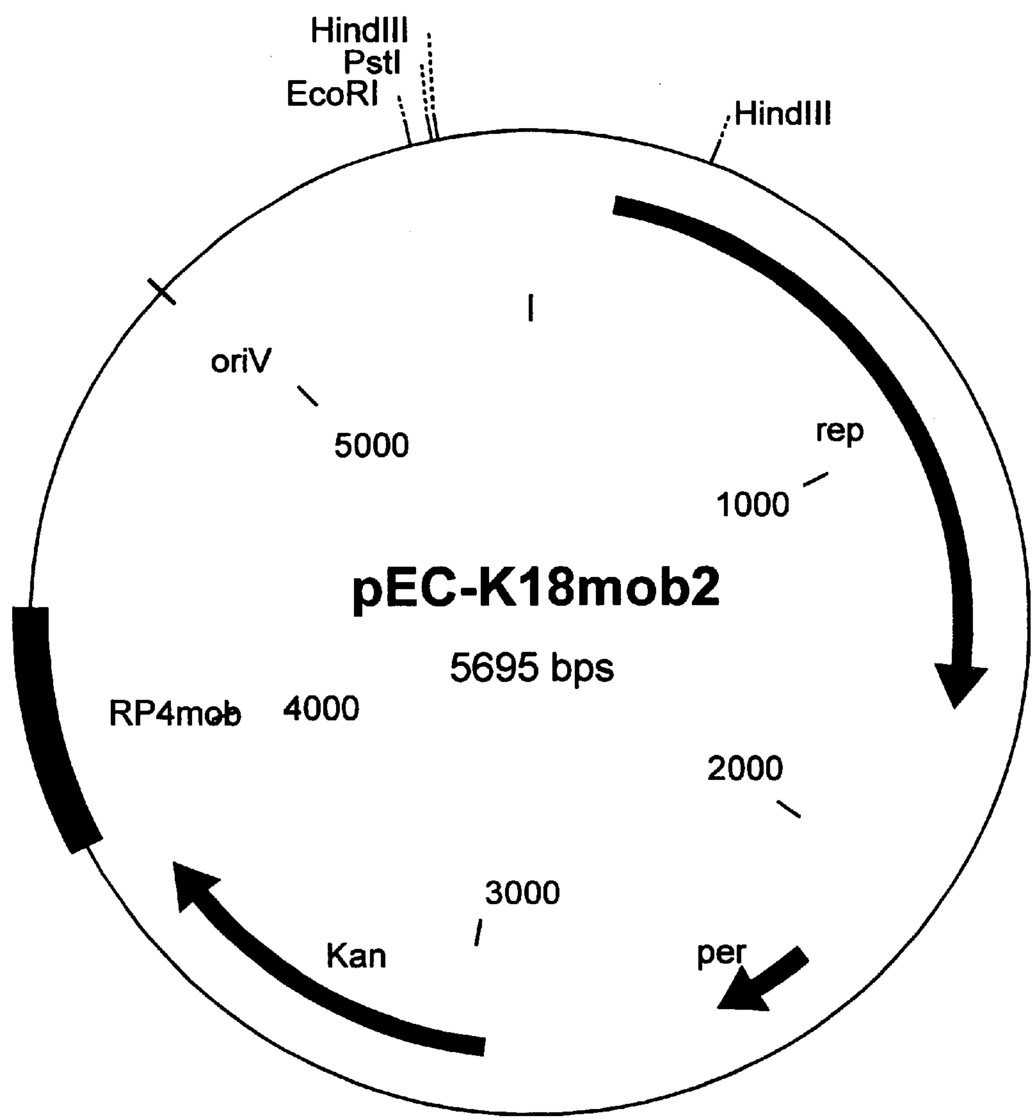

Figure 2: Plasmid pEC-K18mob2ptsIexp
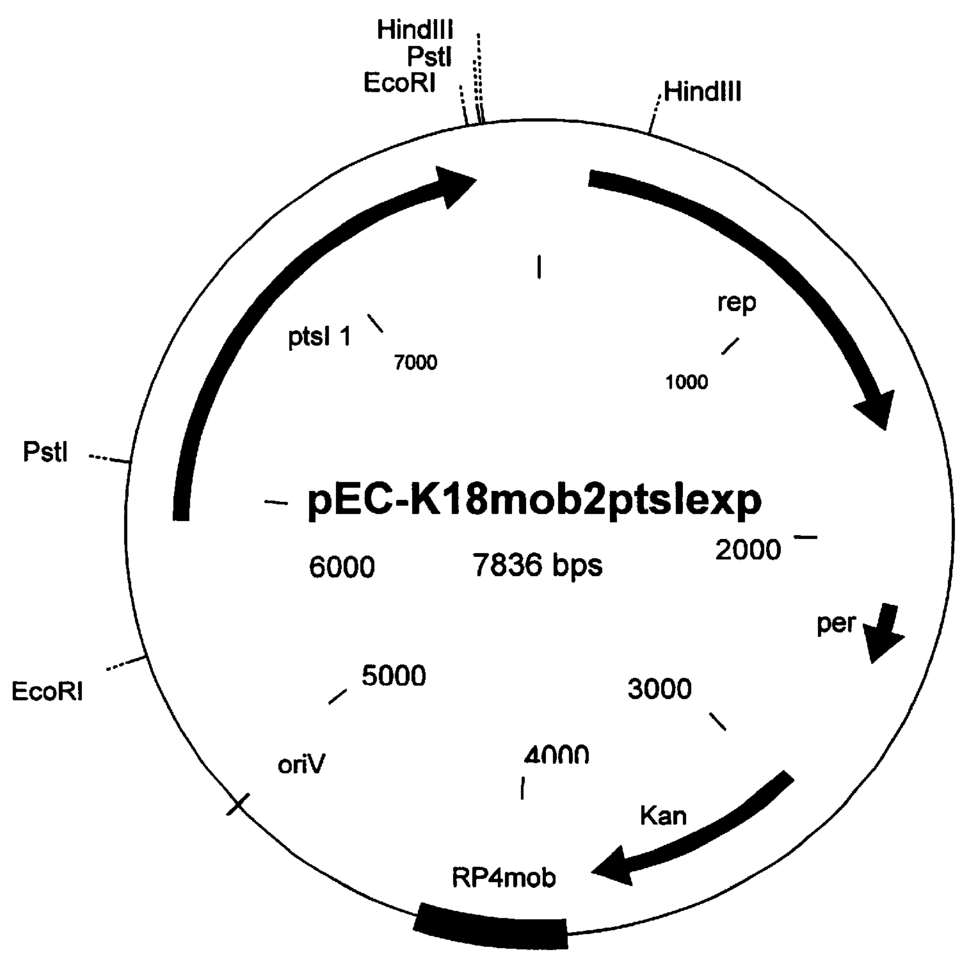

```
                             SEQUENCE LISTING

<160> NUMBER OF SEQ ID NOS: 9

<210> SEQ ID NO 1
<211> LENGTH: 2005
<212> TYPE: DNA
<213> ORGANISM: Corynebacterium glutamicum
<220> FEATURE:
<221> NAME/KEY: CDS
<222> LOCATION: (154)..(1857)
<223> OTHER INFORMATION:

<400> SEQUENCE: 1

gacgatggtc tcaacgtatg aaatatggtg atcgcttaac aacacgctat gttgatatgt      60

gtttgtttgt caatatccaa atgtttgaat agttgcacaa ctgttggttt tgtggtgatc     120

ttgaggaaat taactcaatg attgtgagga tgg gtg gct act gtg gct gat gtg      174
                                     Val Ala Thr Val Ala Asp Val
                                     1               5

aat caa gac act gta ctg aag ggc acc ggc gtt gtc ggt gga gtc cgt       222
Asn Gln Asp Thr Val Leu Lys Gly Thr Gly Val Val Gly Gly Val Arg
        10                  15                  20

tat gca agc gcg gtg tgg att acc cca cgc ccc gaa cta ccc caa gca       270
Tyr Ala Ser Ala Val Trp Ile Thr Pro Arg Pro Glu Leu Pro Gln Ala
    25                  30                  35

ggc gaa gtc gtc gcc gaa gaa aac cgt gaa gca gag cag gag cgt ttc       318
Gly Glu Val Val Ala Glu Glu Asn Arg Glu Ala Glu Gln Glu Arg Phe
40                  45                  50                  55

gac gcc gct gca gcc aca gtc tct tct cgt ttg ctt gag cgc tcc gaa       366
Asp Ala Ala Ala Ala Thr Val Ser Ser Arg Leu Leu Glu Arg Ser Glu
                60                  65                  70

gct gct gaa gga cca gca gct gag gtg ctt aaa gct act gct ggc atg       414
Ala Ala Glu Gly Pro Ala Ala Glu Val Leu Lys Ala Thr Ala Gly Met
            75                  80                  85

gtc aat gac cgt ggc tgg cgt aag gct gtc atc aag ggt gtc aag ggt       462
Val Asn Asp Arg Gly Trp Arg Lys Ala Val Ile Lys Gly Val Lys Gly
        90                  95                  100

ggt cac cct gcg gaa tac gcc gtg gtt gca gca aca acc aag ttc atc       510
Gly His Pro Ala Glu Tyr Ala Val Val Ala Ala Thr Thr Lys Phe Ile
    105                 110                 115

tcc atg ttc aaa gcc gca ggc ggc ctg atc gcg gag cgc acc aca gac       558
Ser Met Phe Lys Ala Ala Gly Gly Leu Ile Ala Glu Arg Thr Thr Asp
120                 125                 130                 135

ttg cgc gac atc cgc gac cgc gtc atc gca gaa ctt cgt ggc gat gaa       606
```

-continued

```
Leu Arg Asp Ile Arg Asp Arg Val Ile Ala Glu Leu Arg Gly Asp Glu
                140                 145                 150

gag cca ggt ctg cca gct gtt tcc gga cag gtc att ctc ttt gca gat      654
Glu Pro Gly Leu Pro Ala Val Ser Gly Gln Val Ile Leu Phe Ala Asp
            155                 160                 165

gac ctc tcc cca gca gac acc gcg gca cta gac aca gat ctc ttt gtg      702
Asp Leu Ser Pro Ala Asp Thr Ala Ala Leu Asp Thr Asp Leu Phe Val
        170                 175                 180

gga ctt gtc act gag ctg ggt ggc cca acg agc cac acc gcg atc atc      750
Gly Leu Val Thr Glu Leu Gly Gly Pro Thr Ser His Thr Ala Ile Ile
    185                 190                 195

gca cgc cag ctc aac gtg cct tgc atc gtc gca tcc ggc gcc ggc atc      798
Ala Arg Gln Leu Asn Val Pro Cys Ile Val Ala Ser Gly Ala Gly Ile
200                 205                 210                 215

aag gac atc aag tcc ggc gaa aag gtg ctt atc gac ggc agc ctc ggc      846
Lys Asp Ile Lys Ser Gly Glu Lys Val Leu Ile Asp Gly Ser Leu Gly
                220                 225                 230

acc att gac cgc aac gcg gac gaa gct gaa gca acc aag ctc gtc tcc      894
Thr Ile Asp Arg Asn Ala Asp Glu Ala Glu Ala Thr Lys Leu Val Ser
            235                 240                 245

gag tcc ctc gag cgc gct gct cgc atc gcc gag tgg aag ggt cct gca      942
Glu Ser Leu Glu Arg Ala Ala Arg Ile Ala Glu Trp Lys Gly Pro Ala
        250                 255                 260

caa acc aag gac ggc tac cgc gtt cag ctg ttg gcc aac gtc caa gac      990
Gln Thr Lys Asp Gly Tyr Arg Val Gln Leu Leu Ala Asn Val Gln Asp
    265                 270                 275

ggc aac tct gca cag cag gct gca cag acc gaa gca gaa ggc atc ggc     1038
Gly Asn Ser Ala Gln Gln Ala Ala Gln Thr Glu Ala Glu Gly Ile Gly
280                 285                 290                 295

ctg ttc cgc acc gaa ctg tgc ttc ctt tcc gcc acc gaa gag cca agc     1086
Leu Phe Arg Thr Glu Leu Cys Phe Leu Ser Ala Thr Glu Glu Pro Ser
                300                 305                 310

gtt gat gag cag gct gcg gtc tac tca aag gtg ctt gaa gca ttc cca     1134
Val Asp Glu Gln Ala Ala Val Tyr Ser Lys Val Leu Glu Ala Phe Pro
            315                 320                 325

gag tcc aag gtc gtt gtc cgc tcc ctc gac gca ggt tct gac aag cca     1182
Glu Ser Lys Val Val Val Arg Ser Leu Asp Ala Gly Ser Asp Lys Pro
        330                 335                 340

gtt cca ttc gca tcg atg gct gat gag atg aac cca gca ctg ggt gtt     1230
Val Pro Phe Ala Ser Met Ala Asp Glu Met Asn Pro Ala Leu Gly Val
    345                 350                 355

cgt ggc ctg cgt atc gca cgt gga cag gtt gat ctg ctg act cgc cag     1278
Arg Gly Leu Arg Ile Ala Arg Gly Gln Val Asp Leu Leu Thr Arg Gln
360                 365                 370                 375

ctc gac gca att gcg aag gcc agc gaa gaa ctc ggc cgt ggc gac gac     1326
Leu Asp Ala Ile Ala Lys Ala Ser Glu Glu Leu Gly Arg Gly Asp Asp
                380                 385                 390

gcc cca acc tgg gtt atg gct cca atg gtg gct acc gct tat gaa gca     1374
Ala Pro Thr Trp Val Met Ala Pro Met Val Ala Thr Ala Tyr Glu Ala
            395                 400                 405

aag tgg ttt gct gac atg tgc cgt gag cgt ggc cta atc gcc ggc gcc     1422
Lys Trp Phe Ala Asp Met Cys Arg Glu Arg Gly Leu Ile Ala Gly Ala
        410                 415                 420

atg atc gaa gtt cca gca gca tcc ctg atg gca gac aag atc atg cct     1470
Met Ile Glu Val Pro Ala Ala Ser Leu Met Ala Asp Lys Ile Met Pro
    425                 430                 435

cac ctg gac ttt gtt tcc atc ggt acc aac gac ctg acc cag tac acc     1518
His Leu Asp Phe Val Ser Ile Gly Thr Asn Asp Leu Thr Gln Tyr Thr
440                 445                 450                 455
```

-continued

```
atg gca gcg gac cgc atg tct cct gag ctt gcc tac ctg acc gat cct      1566
Met Ala Ala Asp Arg Met Ser Pro Glu Leu Ala Tyr Leu Thr Asp Pro
                460                 465                 470

tgg cag cca gca gtc ctg cgc ctg atc aag cac acc tgt gac gaa ggt      1614
Trp Gln Pro Ala Val Leu Arg Leu Ile Lys His Thr Cys Asp Glu Gly
            475                 480                 485

gct cgc ttt aac acc ccg gtc ggt gtt tgt ggt gaa gca gca gca gac      1662
Ala Arg Phe Asn Thr Pro Val Gly Val Cys Gly Glu Ala Ala Ala Asp
        490                 495                 500

cca ctg ttg gca act gtc ctc acc ggt ctt ggc gtg aac tcc ctg tcc      1710
Pro Leu Leu Ala Thr Val Leu Thr Gly Leu Gly Val Asn Ser Leu Ser
    505                 510                 515

gca gca tcc act gct ctc gca gca gtc ggt gca aag ctg tca gag gtc      1758
Ala Ala Ser Thr Ala Leu Ala Ala Val Gly Ala Lys Leu Ser Glu Val
520                 525                 530                 535

acc ctg gaa acc tgt aag aag gca gca gaa gca gca ctt gac gct gaa      1806
Thr Leu Glu Thr Cys Lys Lys Ala Ala Glu Ala Ala Leu Asp Ala Glu
                540                 545                 550

ggt gca act gaa gca cgc gat gct gta cgc gca gtg atc gac gca gca      1854
Gly Ala Thr Glu Ala Arg Asp Ala Val Arg Ala Val Ile Asp Ala Ala
            555                 560                 565

gtc taaaccactg ttgagctaaa aagcctcaaa ttcctgtgtg ggaatttgag          1907
Val
gctttttgcg tggtctaaag cgatttgatg accacgtgct ccgcccgaag cttatcgggt   1967

gtgggaatgt agttgtccca ctcactgcct tcagcgtt                            2005


<210> SEQ ID NO 2
<211> LENGTH: 568
<212> TYPE: PRT
<213> ORGANISM: Corynebacterium glutamicum

<400> SEQUENCE: 2

Val Ala Thr Val Ala Asp Val Asn Gln Asp Thr Val Leu Lys Gly Thr
1               5                   10                  15

Gly Val Val Gly Gly Val Arg Tyr Ala Ser Ala Val Trp Ile Thr Pro
            20                  25                  30

Arg Pro Glu Leu Pro Gln Ala Gly Glu Val Val Ala Glu Glu Asn Arg
        35                  40                  45

Glu Ala Glu Gln Glu Arg Phe Asp Ala Ala Ala Ala Thr Val Ser Ser
    50                  55                  60

Arg Leu Leu Glu Arg Ser Glu Ala Ala Glu Gly Pro Ala Ala Glu Val
65                  70                  75                  80

Leu Lys Ala Thr Ala Gly Met Val Asn Asp Arg Gly Trp Arg Lys Ala
                85                  90                  95

Val Ile Lys Gly Val Lys Gly Gly His Pro Ala Glu Tyr Ala Val Val
            100                 105                 110

Ala Ala Thr Thr Lys Phe Ile Ser Met Phe Lys Ala Ala Gly Gly Leu
        115                 120                 125

Ile Ala Glu Arg Thr Thr Asp Leu Arg Asp Ile Arg Asp Arg Val Ile
    130                 135                 140

Ala Glu Leu Arg Gly Asp Glu Glu Pro Gly Leu Pro Ala Val Ser Gly
145                 150                 155                 160

Gln Val Ile Leu Phe Ala Asp Asp Leu Ser Pro Ala Asp Thr Ala Ala
                165                 170                 175

Leu Asp Thr Asp Leu Phe Val Gly Leu Val Thr Glu Leu Gly Gly Pro
            180                 185                 190

Thr Ser His Thr Ala Ile Ile Ala Arg Gln Leu Asn Val Pro Cys Ile
```

-continued

```
        195                 200                 205

Val Ala Ser Gly Ala Gly Ile Lys Asp Ile Lys Ser Gly Glu Lys Val
    210                 215                 220

Leu Ile Asp Gly Ser Leu Gly Thr Ile Asp Arg Asn Ala Asp Glu Ala
225                 230                 235                 240

Glu Ala Thr Lys Leu Val Ser Glu Ser Leu Glu Arg Ala Ala Arg Ile
                245                 250                 255

Ala Glu Trp Lys Gly Pro Ala Gln Thr Lys Asp Gly Tyr Arg Val Gln
            260                 265                 270

Leu Leu Ala Asn Val Gln Asp Gly Asn Ser Ala Gln Gln Ala Ala Gln
        275                 280                 285

Thr Glu Ala Glu Gly Ile Gly Leu Phe Arg Thr Glu Leu Cys Phe Leu
    290                 295                 300

Ser Ala Thr Glu Glu Pro Ser Val Asp Glu Gln Ala Ala Val Tyr Ser
305                 310                 315                 320

Lys Val Leu Glu Ala Phe Pro Glu Ser Lys Val Val Val Arg Ser Leu
                325                 330                 335

Asp Ala Gly Ser Asp Lys Pro Val Pro Phe Ala Ser Met Ala Asp Glu
            340                 345                 350

Met Asn Pro Ala Leu Gly Val Arg Gly Leu Arg Ile Ala Arg Gly Gln
        355                 360                 365

Val Asp Leu Leu Thr Arg Gln Leu Asp Ala Ile Ala Lys Ala Ser Glu
    370                 375                 380

Glu Leu Gly Arg Gly Asp Asp Ala Pro Thr Trp Val Met Ala Pro Met
385                 390                 395                 400

Val Ala Thr Ala Tyr Glu Ala Lys Trp Phe Ala Asp Met Cys Arg Glu
                405                 410                 415

Arg Gly Leu Ile Ala Gly Ala Met Ile Glu Val Pro Ala Ala Ser Leu
            420                 425                 430

Met Ala Asp Lys Ile Met Pro His Leu Asp Phe Val Ser Ile Gly Thr
        435                 440                 445

Asn Asp Leu Thr Gln Tyr Thr Met Ala Ala Asp Arg Met Ser Pro Glu
    450                 455                 460

Leu Ala Tyr Leu Thr Asp Pro Trp Gln Pro Ala Val Leu Arg Leu Ile
465                 470                 475                 480

Lys His Thr Cys Asp Glu Gly Ala Arg Phe Asn Thr Pro Val Gly Val
                485                 490                 495

Cys Gly Glu Ala Ala Ala Asp Pro Leu Leu Ala Thr Val Leu Thr Gly
            500                 505                 510

Leu Gly Val Asn Ser Leu Ser Ala Ala Ser Thr Ala Leu Ala Ala Val
        515                 520                 525

Gly Ala Lys Leu Ser Glu Val Thr Leu Glu Thr Cys Lys Lys Ala Ala
    530                 535                 540

Glu Ala Ala Leu Asp Ala Glu Gly Ala Thr Glu Ala Arg Asp Ala Val
545                 550                 555                 560

Arg Ala Val Ile Asp Ala Ala Val
                565

<210> SEQ ID NO 3
<211> LENGTH: 2005
<212> TYPE: DNA
<213> ORGANISM: Corynebacterium glutamicum
<220> FEATURE:
<221> NAME/KEY: CDS
<222> LOCATION: (154)..(1857)
```

```
<223> OTHER INFORMATION:

<400> SEQUENCE: 3

gacgatggtc tcaacgtatg aaatatggtg atcgcttaac aacacgctat gttgatatgt     60

gtttgtttgt caatatccaa atgtttgaat agttgcacaa ctgttggttt tgtggtgatc    120

ttgaggaaat taactcaatg attgtgagga tgg gtg gct act gtg gct gat gtg     174
                                     Val Ala Thr Val Ala Asp Val
                                     1               5

aat caa gac act gta ctg aag ggc acc ggc gtt gtc ggt gga gtc cgt      222
Asn Gln Asp Thr Val Leu Lys Gly Thr Gly Val Val Gly Gly Val Arg
        10                  15                  20

tat gca agc gcg gtg tgg att acc cca cgc ccc gaa cta ccc caa gca      270
Tyr Ala Ser Ala Val Trp Ile Thr Pro Arg Pro Glu Leu Pro Gln Ala
    25                  30                  35

ggc gaa gtc gtc gcc gaa gaa aac cgt gaa gca gag cag gag cgt ttc      318
Gly Glu Val Val Ala Glu Glu Asn Arg Glu Ala Glu Gln Glu Arg Phe
40                  45                  50                  55

gac gcc gct gca gcc aca gtc tct tct cgt ttg ctt gag cgc tcc gaa      366
Asp Ala Ala Ala Ala Thr Val Ser Ser Arg Leu Leu Glu Arg Ser Glu
                60                  65                  70

gct gct gaa gga cca gca gct gag gtg ctt aaa gct act gct ggc atg      414
Ala Ala Glu Gly Pro Ala Ala Glu Val Leu Lys Ala Thr Ala Gly Met
            75                  80                  85

gtc aat gac cgt ggc tgg cgt aag gct gtc atc aag ggt gtc aag ggt      462
Val Asn Asp Arg Gly Trp Arg Lys Ala Val Ile Lys Gly Val Lys Gly
        90                  95                  100

ggt cac cct gcg gaa tac gcc gtg gtt gca gca aca acc aag ttc atc      510
Gly His Pro Ala Glu Tyr Ala Val Val Ala Ala Thr Thr Lys Phe Ile
    105                 110                 115

tcc atg ttc gaa gcc gca ggc ggc ctg atc gcg gag cgc acc aca gac      558
Ser Met Phe Glu Ala Ala Gly Gly Leu Ile Ala Glu Arg Thr Thr Asp
120                 125                 130                 135

ttg tgc gac atc cgc gac cgc gtc atc gca gaa ctt cgt ggc gat gaa      606
Leu Cys Asp Ile Arg Asp Arg Val Ile Ala Glu Leu Arg Gly Asp Glu
                140                 145                 150

gag cca ggt ctg cca gct gtt tcc gga cag gtc att ctc ttt gca gat      654
Glu Pro Gly Leu Pro Ala Val Ser Gly Gln Val Ile Leu Phe Ala Asp
            155                 160                 165

gac ctc tcc cca gca gac acc gcg gca cta gac aca gat ctc ttt gtg      702
Asp Leu Ser Pro Ala Asp Thr Ala Ala Leu Asp Thr Asp Leu Phe Val
        170                 175                 180

gga ctt gtc act gag ctg ggt ggc cca acg agc cac acc gcg atc atc      750
Gly Leu Val Thr Glu Leu Gly Gly Pro Thr Ser His Thr Ala Ile Ile
    185                 190                 195

gca cgc cag ctc aac gtg cct tgc atc gtc gca tcc ggc gcc ggc atc      798
Ala Arg Gln Leu Asn Val Pro Cys Ile Val Ala Ser Gly Ala Gly Ile
200                 205                 210                 215

aag gac atc aag tcc ggc gaa aag gtg ctt atc gac ggc agc ctc ggc      846
Lys Asp Ile Lys Ser Gly Glu Lys Val Leu Ile Asp Gly Ser Leu Gly
                220                 225                 230

acc att gac cgc aac gcg gac gaa gct gaa gca acc aag ctc gtc tcc      894
Thr Ile Asp Arg Asn Ala Asp Glu Ala Glu Ala Thr Lys Leu Val Ser
            235                 240                 245

gag tcc ctc gag cgc gct gct cgc atc gcc gag tgg aag ggt cct gca      942
Glu Ser Leu Glu Arg Ala Ala Arg Ile Ala Glu Trp Lys Gly Pro Ala
        250                 255                 260

caa acc aag gac ggc tac cgc gtt cag ctg ttg gcc aac gtc caa gac      990
Gln Thr Lys Asp Gly Tyr Arg Val Gln Leu Leu Ala Asn Val Gln Asp
    265                 270                 275
```

-continued

```
ggc aac tct gca cag cag gct gca cag acc gaa gca gaa ggc atc ggc     1038
Gly Asn Ser Ala Gln Gln Ala Ala Gln Thr Glu Ala Glu Gly Ile Gly
280                 285                 290                 295

ctg ttc cgc acc gaa ctg tgc ttc ctt tcc gcc acc gaa gag cca agc     1086
Leu Phe Arg Thr Glu Leu Cys Phe Leu Ser Ala Thr Glu Glu Pro Ser
                300                 305                 310

gtt gat gag cag gct gcg gtc tac tca aag gtg ctt gaa gca ttc cca     1134
Val Asp Glu Gln Ala Ala Val Tyr Ser Lys Val Leu Glu Ala Phe Pro
            315                 320                 325

gag tcc aag gtc gtt gtc cgc tcc ctc gac gca ggt tct gac aag cca     1182
Glu Ser Lys Val Val Val Arg Ser Leu Asp Ala Gly Ser Asp Lys Pro
        330                 335                 340

gtt cca ttc gca tcg atg gct gat gag atg aac cca gca ctg ggt gtt     1230
Val Pro Phe Ala Ser Met Ala Asp Glu Met Asn Pro Ala Leu Gly Val
    345                 350                 355

cgt ggc ctg cgt atc gca cgt gga cag gtt gat ctg ctg act cgc cag     1278
Arg Gly Leu Arg Ile Ala Arg Gly Gln Val Asp Leu Leu Thr Arg Gln
360                 365                 370                 375

ctc gac gca att gcg aag gcc agc gaa gaa ctc ggc cgt ggc gac gac     1326
Leu Asp Ala Ile Ala Lys Ala Ser Glu Glu Leu Gly Arg Gly Asp Asp
                380                 385                 390

gcc cca acc tgg gtt atg gct cca atg gtg gct acc gct tat gaa gca     1374
Ala Pro Thr Trp Val Met Ala Pro Met Val Ala Thr Ala Tyr Glu Ala
            395                 400                 405

aag tgg ttt gct gac atg tgc cgt gag cgt ggc cta atc gcc ggc gcc     1422
Lys Trp Phe Ala Asp Met Cys Arg Glu Arg Gly Leu Ile Ala Gly Ala
        410                 415                 420

atg atc gaa gtt cca gca gca tcc ctg atg gca gac aag atc atg cct     1470
Met Ile Glu Val Pro Ala Ala Ser Leu Met Ala Asp Lys Ile Met Pro
    425                 430                 435

cac ctg gac ttt gtt tcc atc ggt acc aac gac ctg acc cag tac acc     1518
His Leu Asp Phe Val Ser Ile Gly Thr Asn Asp Leu Thr Gln Tyr Thr
440                 445                 450                 455

atg gca gcg gac cgc atg tct cct gag ctt gcc tac ctg acc gat cct     1566
Met Ala Ala Asp Arg Met Ser Pro Glu Leu Ala Tyr Leu Thr Asp Pro
                460                 465                 470

tgg cag cca gca gtc ctg cgc ctg atc aag cac acc tgt gac gaa ggt     1614
Trp Gln Pro Ala Val Leu Arg Leu Ile Lys His Thr Cys Asp Glu Gly
            475                 480                 485

gct cgc ttt aac acc ccg gtc ggt gtt tgt ggt gaa gca gca gca gac     1662
Ala Arg Phe Asn Thr Pro Val Gly Val Cys Gly Glu Ala Ala Ala Asp
        490                 495                 500

cca ctg ttg gca act gtc ctc acc ggt ctt ggc gtg aac tcc ctg tcc     1710
Pro Leu Leu Ala Thr Val Leu Thr Gly Leu Gly Val Asn Ser Leu Ser
    505                 510                 515

gca gca tcc act gct ctc gca gca gtc ggt gca aag ctg tca gag gtc     1758
Ala Ala Ser Thr Ala Leu Ala Ala Val Gly Ala Lys Leu Ser Glu Val
520                 525                 530                 535

acc ctg gaa acc tgt aag aag gca gca gaa gca gca ctt gac gct gaa     1806
Thr Leu Glu Thr Cys Lys Lys Ala Ala Glu Ala Ala Leu Asp Ala Glu
                540                 545                 550

ggt gca act gaa gca cgc gat gct gta cgc gca gtg atc gac gca gca     1854
Gly Ala Thr Glu Ala Arg Asp Ala Val Arg Ala Val Ile Asp Ala Ala
            555                 560                 565

gtc taaaccactg ttgagctaaa aagcctcaaa ttcctgtgtg ggaatttgag          1907
Val

gctttttgcg tggtctaaag cgatttgatg accacgtgct ccgcccgaag cttatcgggt   1967

gtgggaatgt agttgtccca ctcactgcct tcagcgtt                           2005
```

```
<210> SEQ ID NO 4
<211> LENGTH: 568
<212> TYPE: PRT
<213> ORGANISM: Corynebacterium glutamicum

<400> SEQUENCE: 4

Val Ala Thr Val Ala Asp Val Asn Gln Asp Thr Val Leu Lys Gly Thr
1               5                   10                  15

Gly Val Val Gly Gly Val Arg Tyr Ala Ser Ala Val Trp Ile Thr Pro
            20                  25                  30

Arg Pro Glu Leu Pro Gln Ala Gly Glu Val Val Ala Glu Glu Asn Arg
        35                  40                  45

Glu Ala Glu Gln Glu Arg Phe Asp Ala Ala Ala Ala Thr Val Ser Ser
    50                  55                  60

Arg Leu Leu Glu Arg Ser Glu Ala Ala Glu Gly Pro Ala Ala Glu Val
65                  70                  75                  80

Leu Lys Ala Thr Ala Gly Met Val Asn Asp Arg Gly Trp Arg Lys Ala
                85                  90                  95

Val Ile Lys Gly Val Lys Gly Gly His Pro Ala Glu Tyr Ala Val Val
            100                 105                 110

Ala Ala Thr Thr Lys Phe Ile Ser Met Phe Glu Ala Ala Gly Gly Leu
        115                 120                 125

Ile Ala Glu Arg Thr Thr Asp Leu Cys Asp Ile Arg Asp Arg Val Ile
    130                 135                 140

Ala Glu Leu Arg Gly Asp Glu Glu Pro Gly Leu Pro Ala Val Ser Gly
145                 150                 155                 160

Gln Val Ile Leu Phe Ala Asp Asp Leu Ser Pro Ala Asp Thr Ala Ala
                165                 170                 175

Leu Asp Thr Asp Leu Phe Val Gly Leu Val Thr Glu Leu Gly Gly Pro
            180                 185                 190

Thr Ser His Thr Ala Ile Ile Ala Arg Gln Leu Asn Val Pro Cys Ile
        195                 200                 205

Val Ala Ser Gly Ala Gly Ile Lys Asp Ile Lys Ser Gly Glu Lys Val
    210                 215                 220

Leu Ile Asp Gly Ser Leu Gly Thr Ile Asp Arg Asn Ala Asp Glu Ala
225                 230                 235                 240

Glu Ala Thr Lys Leu Val Ser Glu Ser Leu Glu Arg Ala Ala Arg Ile
                245                 250                 255

Ala Glu Trp Lys Gly Pro Ala Gln Thr Lys Asp Gly Tyr Arg Val Gln
            260                 265                 270

Leu Leu Ala Asn Val Gln Asp Gly Asn Ser Ala Gln Gln Ala Ala Gln
        275                 280                 285

Thr Glu Ala Glu Gly Ile Gly Leu Phe Arg Thr Glu Leu Cys Phe Leu
    290                 295                 300

Ser Ala Thr Glu Glu Pro Ser Val Asp Glu Gln Ala Ala Val Tyr Ser
305                 310                 315                 320

Lys Val Leu Glu Ala Phe Pro Glu Ser Lys Val Val Val Arg Ser Leu
                325                 330                 335

Asp Ala Gly Ser Asp Lys Pro Val Pro Phe Ala Ser Met Ala Asp Glu
            340                 345                 350

Met Asn Pro Ala Leu Gly Val Arg Gly Leu Arg Ile Ala Arg Gly Gln
        355                 360                 365

Val Asp Leu Leu Thr Arg Gln Leu Asp Ala Ile Ala Lys Ala Ser Glu
```

-continued

```
    370                 375                 380

Glu Leu Gly Arg Gly Asp Asp Ala Pro Thr Trp Val Met Ala Pro Met
385                 390                 395                 400

Val Ala Thr Ala Tyr Glu Ala Lys Trp Phe Ala Asp Met Cys Arg Glu
                405                 410                 415

Arg Gly Leu Ile Ala Gly Ala Met Ile Glu Val Pro Ala Ala Ser Leu
            420                 425                 430

Met Ala Asp Lys Ile Met Pro His Leu Asp Phe Val Ser Ile Gly Thr
        435                 440                 445

Asn Asp Leu Thr Gln Tyr Thr Met Ala Ala Asp Arg Met Ser Pro Glu
    450                 455                 460

Leu Ala Tyr Leu Thr Asp Pro Trp Gln Pro Ala Val Leu Arg Leu Ile
465                 470                 475                 480

Lys His Thr Cys Asp Glu Gly Ala Arg Phe Asn Thr Pro Val Gly Val
                485                 490                 495

Cys Gly Glu Ala Ala Ala Asp Pro Leu Leu Ala Thr Val Leu Thr Gly
            500                 505                 510

Leu Gly Val Asn Ser Leu Ser Ala Ala Ser Thr Ala Leu Ala Ala Val
        515                 520                 525

Gly Ala Lys Leu Ser Glu Val Thr Leu Glu Thr Cys Lys Lys Ala Ala
    530                 535                 540

Glu Ala Ala Leu Asp Ala Glu Gly Ala Thr Glu Ala Arg Asp Ala Val
545                 550                 555                 560

Arg Ala Val Ile Asp Ala Ala Val
                565


<210> SEQ ID NO 5
<211> LENGTH: 293
<212> TYPE: DNA
<213> ORGANISM: Corynebacterium glutamicum

<400> SEQUENCE: 5

aagaagcaat tgcatgctgt ctttccgttt ggctgaccat gcttaacctc gctgatgttg     60

gagttggtgt tgacgtggaa gaaattttgt tcaagcggga aactggtttt tgaccagtgt    120

tgttttggtt ccgattgtgg aagaaccgta tgaagttatt aaaagtgctg gttaaagcgg    180

aaaatctaaa ataaatcgag cggaaaacac atgatgtggc ctcagtcact atgatggaga    240

aggtgttaaa tctccttcaa atgcattgat aagctggtgg aatatcaact tgt           293


<210> SEQ ID NO 6
<211> LENGTH: 2298
<212> TYPE: DNA
<213> ORGANISM: Corynebacterium glutamicum
<220> FEATURE:
<221> NAME/KEY: CDS
<222> LOCATION: (447)..(2150)
<223> OTHER INFORMATION:

<400> SEQUENCE: 6

aagaagcaat tgcatgctgt ctttccgttt ggctgaccat gcttaacctc gctgatgttg     60

gagttggtgt tgacgtggaa gaaattttgt tcaagcggga aactggtttt tgaccagtgt    120

tgttttggtt ccgattgtgg aagaaccgta tgaagttatt aaaagtgctg gttaaagcgg    180

aaaatctaaa ataaatcgag cggaaaacac atgatgtggc ctcagtcact atgatggaga    240

aggtgttaaa tctccttcaa atgcattgat aagctggtgg aatatcaact tgtgacgatg    300

gtctcaacgt atgaaatatg gtgatcgctt aacaacacgc tatgttgata tgtgtttgtt    360
```

-continued

```
tgtcaatatc caaatgtttg aatagttgca caactgttgg ttttgtggtg atcttgagga    420

aattaactca atgattgtga ggatgg gtg gct act gtg gct gat gtg aat caa     473
                             Val Ala Thr Val Ala Asp Val Asn Gln
                             1               5

gac act gta ctg aag ggc acc ggc gtt gtc ggt gga gtc cgt tat gca      521
Asp Thr Val Leu Lys Gly Thr Gly Val Val Gly Gly Val Arg Tyr Ala
10                  15                  20                  25

agc gcg gtg tgg att acc cca cgc ccc gaa cta ccc caa gca ggc gaa      569
Ser Ala Val Trp Ile Thr Pro Arg Pro Glu Leu Pro Gln Ala Gly Glu
                30                  35                  40

gtc gtc gcc gaa gaa aac cgt gaa gca gag cag gag cgt ttc gac gcc      617
Val Val Ala Glu Glu Asn Arg Glu Ala Glu Gln Glu Arg Phe Asp Ala
            45                  50                  55

gct gca gcc aca gtc tct tct cgt ttg ctt gag cgc tcc gaa gct gct      665
Ala Ala Ala Thr Val Ser Ser Arg Leu Leu Glu Arg Ser Glu Ala Ala
        60                  65                  70

gaa gga cca gca gct gag gtg ctt aaa gct act gct ggc atg gtc aat      713
Glu Gly Pro Ala Ala Glu Val Leu Lys Ala Thr Ala Gly Met Val Asn
    75                  80                  85

gac cgt ggc tgg cgt aag gct gtc atc aag ggt gtc aag ggt ggt cac      761
Asp Arg Gly Trp Arg Lys Ala Val Ile Lys Gly Val Lys Gly Gly His
90                  95                  100                 105

cct gcg gaa tac gcc gtg gtt gca gca aca acc aag ttc atc tcc atg      809
Pro Ala Glu Tyr Ala Val Val Ala Ala Thr Thr Lys Phe Ile Ser Met
                110                 115                 120

ttc aaa gcc gca ggc ggc ctg atc gcg gag cgc acc aca gac ttg cgc      857
Phe Lys Ala Ala Gly Gly Leu Ile Ala Glu Arg Thr Thr Asp Leu Arg
            125                 130                 135

gac atc cgc gac cgc gtc atc gca gaa ctt cgt ggc gat gaa gag cca      905
Asp Ile Arg Asp Arg Val Ile Ala Glu Leu Arg Gly Asp Glu Glu Pro
        140                 145                 150

ggt ctg cca gct gtt tcc gga cag gtc att ctc ttt gca gat gac ctc      953
Gly Leu Pro Ala Val Ser Gly Gln Val Ile Leu Phe Ala Asp Asp Leu
    155                 160                 165

tcc cca gca gac acc gcg gca cta gac aca gat ctc ttt gtg gga ctt     1001
Ser Pro Ala Asp Thr Ala Ala Leu Asp Thr Asp Leu Phe Val Gly Leu
170                 175                 180                 185

gtc act gag ctg ggt ggc cca acg agc cac acc gcg atc atc gca cgc     1049
Val Thr Glu Leu Gly Gly Pro Thr Ser His Thr Ala Ile Ile Ala Arg
                190                 195                 200

cag ctc aac gtg cct tgc atc gtc gca tcc ggc gcc ggc atc aag gac     1097
Gln Leu Asn Val Pro Cys Ile Val Ala Ser Gly Ala Gly Ile Lys Asp
            205                 210                 215

atc aag tcc ggc gaa aag gtg ctt atc gac ggc agc ctc ggc acc att     1145
Ile Lys Ser Gly Glu Lys Val Leu Ile Asp Gly Ser Leu Gly Thr Ile
        220                 225                 230

gac cgc aac gcg gac gaa gct gaa gca acc aag ctc gtc tcc gag tcc     1193
Asp Arg Asn Ala Asp Glu Ala Glu Ala Thr Lys Leu Val Ser Glu Ser
    235                 240                 245

ctc gag cgc gct gct cgc atc gcc gag tgg aag ggt cct gca caa acc     1241
Leu Glu Arg Ala Ala Arg Ile Ala Glu Trp Lys Gly Pro Ala Gln Thr
250                 255                 260                 265

aag gac ggc tac cgc gtt cag ctg ttg gcc aac gtc caa gac ggc aac     1289
Lys Asp Gly Tyr Arg Val Gln Leu Leu Ala Asn Val Gln Asp Gly Asn
                270                 275                 280

tct gca cag cag gct gca cag acc gaa gca gaa ggc atc ggc ctg ttc     1337
Ser Ala Gln Gln Ala Ala Gln Thr Glu Ala Glu Gly Ile Gly Leu Phe
            285                 290                 295
```

-continued

```
cgc acc gaa ctg tgc ttc ctt tcc gcc acc gaa gag cca agc gtt gat      1385
Arg Thr Glu Leu Cys Phe Leu Ser Ala Thr Glu Glu Pro Ser Val Asp
        300                 305                 310

gag cag gct gcg gtc tac tca aag gtg ctt gaa gca ttc cca gag tcc      1433
Glu Gln Ala Ala Val Tyr Ser Lys Val Leu Glu Ala Phe Pro Glu Ser
    315                 320                 325

aag gtc gtt gtc cgc tcc ctc gac gca ggt tct gac aag cca gtt cca      1481
Lys Val Val Val Arg Ser Leu Asp Ala Gly Ser Asp Lys Pro Val Pro
330                 335                 340                 345

ttc gca tcg atg gct gat gag atg aac cca gca ctg ggt gtt cgt ggc      1529
Phe Ala Ser Met Ala Asp Glu Met Asn Pro Ala Leu Gly Val Arg Gly
                350                 355                 360

ctg cgt atc gca cgt gga cag gtt gat ctg ctg act cgc cag ctc gac      1577
Leu Arg Ile Ala Arg Gly Gln Val Asp Leu Leu Thr Arg Gln Leu Asp
            365                 370                 375

gca att gcg aag gcc agc gaa gaa ctc ggc cgt ggc gac gac gcc cca      1625
Ala Ile Ala Lys Ala Ser Glu Glu Leu Gly Arg Gly Asp Asp Ala Pro
        380                 385                 390

acc tgg gtt atg gct cca atg gtg gct acc gct tat gaa gca aag tgg      1673
Thr Trp Val Met Ala Pro Met Val Ala Thr Ala Tyr Glu Ala Lys Trp
    395                 400                 405

ttt gct gac atg tgc cgt gag cgt ggc cta atc gcc ggc gcc atg atc      1721
Phe Ala Asp Met Cys Arg Glu Arg Gly Leu Ile Ala Gly Ala Met Ile
410                 415                 420                 425

gaa gtt cca gca gca tcc ctg atg gca gac aag atc atg cct cac ctg      1769
Glu Val Pro Ala Ala Ser Leu Met Ala Asp Lys Ile Met Pro His Leu
                430                 435                 440

gac ttt gtt tcc atc ggt acc aac gac ctg acc cag tac acc atg gca      1817
Asp Phe Val Ser Ile Gly Thr Asn Asp Leu Thr Gln Tyr Thr Met Ala
            445                 450                 455

gcg gac cgc atg tct cct gag ctt gcc tac ctg acc gat cct tgg cag      1865
Ala Asp Arg Met Ser Pro Glu Leu Ala Tyr Leu Thr Asp Pro Trp Gln
        460                 465                 470

cca gca gtc ctg cgc ctg atc aag cac acc tgt gac gaa ggt gct cgc      1913
Pro Ala Val Leu Arg Leu Ile Lys His Thr Cys Asp Glu Gly Ala Arg
    475                 480                 485

ttt aac acc ccg gtc ggt gtt tgt ggt gaa gca gca gca gac cca ctg      1961
Phe Asn Thr Pro Val Gly Val Cys Gly Glu Ala Ala Ala Asp Pro Leu
490                 495                 500                 505

ttg gca act gtc ctc acc ggt ctt ggc gtg aac tcc ctg tcc gca gca      2009
Leu Ala Thr Val Leu Thr Gly Leu Gly Val Asn Ser Leu Ser Ala Ala
                510                 515                 520

tcc act gct ctc gca gca gtc ggt gca aag ctg tca gag gtc acc ctg      2057
Ser Thr Ala Leu Ala Ala Val Gly Ala Lys Leu Ser Glu Val Thr Leu
            525                 530                 535

gaa acc tgt aag aag gca gca gaa gca gca ctt gac gct gaa ggt gca      2105
Glu Thr Cys Lys Lys Ala Ala Glu Ala Ala Leu Asp Ala Glu Gly Ala
        540                 545                 550

act gaa gca cgc gat gct gta cgc gca gtg atc gac gca gca gtc          2150
Thr Glu Ala Arg Asp Ala Val Arg Ala Val Ile Asp Ala Ala Val
    555                 560                 565

taaaccactg ttgagctaaa aagcctcaaa ttcctgtgtg ggaatttgag gctttttgcg   2210

tggtctaaag cgatttgatg accacgtgct ccgcccgaag cttatcgggt gtgggaatgt   2270

agttgtccca ctcactgcct tcagcgtt                                      2298
```

<210> SEQ ID NO 7
<211> LENGTH: 568
<212> TYPE: PRT
<213> ORGANISM: Corynebacterium glutamicum -continued

<400> SEQUENCE: 7

```
Val Ala Thr Val Ala Asp Val Asn Gln Asp Thr Val Leu Lys Gly Thr
1               5                   10                  15

Gly Val Val Gly Gly Val Arg Tyr Ala Ser Ala Val Trp Ile Thr Pro
            20                  25                  30

Arg Pro Glu Leu Pro Gln Ala Gly Glu Val Val Ala Glu Glu Asn Arg
        35                  40                  45

Glu Ala Glu Gln Glu Arg Phe Asp Ala Ala Ala Ala Thr Val Ser Ser
    50                  55                  60

Arg Leu Leu Glu Arg Ser Glu Ala Ala Glu Gly Pro Ala Ala Glu Val
65                  70                  75                  80

Leu Lys Ala Thr Ala Gly Met Val Asn Asp Arg Gly Trp Arg Lys Ala
                85                  90                  95

Val Ile Lys Gly Val Lys Gly Gly His Pro Ala Glu Tyr Ala Val Val
            100                 105                 110

Ala Ala Thr Thr Lys Phe Ile Ser Met Phe Lys Ala Ala Gly Gly Leu
        115                 120                 125

Ile Ala Glu Arg Thr Thr Asp Leu Arg Asp Ile Arg Asp Arg Val Ile
    130                 135                 140

Ala Glu Leu Arg Gly Asp Glu Glu Pro Gly Leu Pro Ala Val Ser Gly
145                 150                 155                 160

Gln Val Ile Leu Phe Ala Asp Asp Leu Ser Pro Ala Asp Thr Ala Ala
                165                 170                 175

Leu Asp Thr Asp Leu Phe Val Gly Leu Val Thr Glu Leu Gly Gly Pro
            180                 185                 190

Thr Ser His Thr Ala Ile Ile Ala Arg Gln Leu Asn Val Pro Cys Ile
        195                 200                 205

Val Ala Ser Gly Ala Gly Ile Lys Asp Ile Lys Ser Gly Glu Lys Val
    210                 215                 220

Leu Ile Asp Gly Ser Leu Gly Thr Ile Asp Arg Asn Ala Asp Glu Ala
225                 230                 235                 240

Glu Ala Thr Lys Leu Val Ser Glu Ser Leu Glu Arg Ala Ala Arg Ile
                245                 250                 255

Ala Glu Trp Lys Gly Pro Ala Gln Thr Lys Asp Gly Tyr Arg Val Gln
            260                 265                 270

Leu Leu Ala Asn Val Gln Asp Gly Asn Ser Ala Gln Gln Ala Ala Gln
        275                 280                 285

Thr Glu Ala Glu Gly Ile Gly Leu Phe Arg Thr Glu Leu Cys Phe Leu
    290                 295                 300

Ser Ala Thr Glu Glu Pro Ser Val Asp Glu Gln Ala Ala Val Tyr Ser
305                 310                 315                 320

Lys Val Leu Glu Ala Phe Pro Glu Ser Lys Val Val Val Arg Ser Leu
                325                 330                 335

Asp Ala Gly Ser Asp Lys Pro Val Pro Phe Ala Ser Met Ala Asp Glu
            340                 345                 350

Met Asn Pro Ala Leu Gly Val Arg Gly Leu Arg Ile Ala Arg Gly Gln
        355                 360                 365

Val Asp Leu Leu Thr Arg Gln Leu Asp Ala Ile Ala Lys Ala Ser Glu
    370                 375                 380

Glu Leu Gly Arg Gly Asp Asp Ala Pro Thr Trp Val Met Ala Pro Met
385                 390                 395                 400

Val Ala Thr Ala Tyr Glu Ala Lys Trp Phe Ala Asp Met Cys Arg Glu
```

-continued

```
                405                 410                 415

Arg Gly Leu Ile Ala Gly Ala Met Ile Glu Val Pro Ala Ala Ser Leu
            420                 425                 430

Met Ala Asp Lys Ile Met Pro His Leu Asp Phe Val Ser Ile Gly Thr
        435                 440                 445

Asn Asp Leu Thr Gln Tyr Thr Met Ala Ala Asp Arg Met Ser Pro Glu
    450                 455                 460

Leu Ala Tyr Leu Thr Asp Pro Trp Gln Pro Ala Val Leu Arg Leu Ile
465                 470                 475                 480

Lys His Thr Cys Asp Glu Gly Ala Arg Phe Asn Thr Pro Val Gly Val
                485                 490                 495

Cys Gly Glu Ala Ala Ala Asp Pro Leu Leu Ala Thr Val Leu Thr Gly
            500                 505                 510

Leu Gly Val Asn Ser Leu Ser Ala Ala Ser Thr Ala Leu Ala Ala Val
        515                 520                 525

Gly Ala Lys Leu Ser Glu Val Thr Leu Glu Thr Cys Lys Lys Ala Ala
    530                 535                 540

Glu Ala Ala Leu Asp Ala Glu Gly Ala Thr Glu Ala Arg Asp Ala Val
545                 550                 555                 560

Arg Ala Val Ile Asp Ala Ala Val
                565


<210> SEQ ID NO 8
<211> LENGTH: 20
<212> TYPE: DNA
<213> ORGANISM: Corynebacterium glutamicum

<400> SEQUENCE: 8

ggctgaccat gcttaacctc                                                  20


<210> SEQ ID NO 9
<211> LENGTH: 20
<212> TYPE: DNA
<213> ORGANISM: Corynebacterium glutamicum

<400> SEQUENCE: 9

agactgctgc gtcgatcact                                                  20
```

NUCLEOTIDE SEQUENCES CODING FOR THE PTSI PROTEIN

CROSS-REFERENCE TO RELATED APPLICATIONS

The present application claims priority to German Application No. DE 10045496.8, which was filed on Sep. 13, 2000, the entire contents of which is incorporated herein by reference.

BACKGROUND OF THE INVENTION

1. Field of the Invention

The present invention provides nucleotide sequences from Coryneform bacteria which code for the PtsI protein and a process for the fermentative preparation of amino acids using bacteria in which the ptsI gene is enhanced.

2. Discussion of the Background

L-Amino acids, in particular L-lysine, are used in human medicine, in the pharmaceuticals industry and in the foodstuffs industry, particularly in animal nutrition.

It is known that amino acids are prepared by fermentation from strains of Coryneform bacteria, in particular *Corynebacterium glutamicum*. Because of their great importance, work is constantly being undertaken to improve amino acid preparations. Improvements can relate to the fermentation means, such as stirring and supply of oxygen; the composition of the nutrient media, such as the sugar concentration during the fermentation; working up the product form, for example, using ion exchange chromatography; or by altering the intrinsic output properties of the microorganism itself.

Methods of mutagenesis and mutant selection are used to improve the output properties of microorganisms. Strains that are resistant to antimetabolites or are auxotrophic for metabolites of regulatory importance and produce amino acids may be obtained in this manner.

Methods of the recombinant DNA technique have also been employed for some years to improve Corynebacterium strains which produce L-amino acid, by amplifying individual amino acid biosynthesis genes and investigating the effect on the amino acid production.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that enhancing the ptsI gene encoding the enzyme phosphotransferase system enzyme I (PtsI) would improve L-amino acid yields.

SUMMARY OF THE INVENTION

One object of the present invention is providing a new process adjuvant for improving the fermentative production of L-amino acids, particularly L-lysine and L-glutamate. Such process adjuvants include enhanced bacteria, preferably enhanced Coryneform bacteria which express enhanced levels of phosphotransferase system enzyme I which is encoded by the ptsI gene.

Thus, another object of the present invention is providing such a bacterium, which expresses enhanced amounts of phosphotransferase system enzyme I or gene products of the ptsI gene.

Another object of the present invention is providing a bacterium, preferably a Coryneform bacterium, which expresses a polypeptide that has enhanced phosphotransferase system enzyme I activity.

Another object of the invention is to provide a nucleotide sequence encoding a polypeptide which has a phosphotransferase system enzyme I sequence. One embodiment of such a sequence is the nucleotide sequence of SEQ ID NO: 1. Other embodiments of the sequence are the nucleotide sequences of SEQ ID NOS:3 and 6.

A further object of the invention is a method of making a phosphotransferase system enzyme I or an isolated polypeptide having phosphotransferase system enzyme I activity, as well as use of such isolated polypeptides in the production of amino acids. One embodiment of such a polypeptide is the polypeptide having the amino acid sequence of SEQ ID NO: 2. Another embodiment of the sequence is the amino acid sequence of SEQ ID NO:4.

In one embodiment the invention provides isolated polypeptides comprising the amino acid sequences in SEQ ID NOS: 2 and 4.

Other objects of the invention include methods of detecting nucleic acid sequences homologous to SEQ ID NO: 1, particularly nucleic acid sequences encoding polypeptides that have the phosphotransferase system enzyme I activity, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWINGS

FIG. 1: Map of the plasmid pEC-K18mob2.

FIG. 2: Map of the plasmid pEC-K18mob2ptsIexp.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Cold Spring Harbor Laboratory, New York (1989), Current Protocols in Molecular Biology, Ausebel et al (eds), John Wiley and Sons, Inc. New York (2000) and the various references cited therein.

"L-amino acids" or "amino acids" as used herein mean one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. Furthermore, the amino acids may be in the base form or salt form, e.g. monochloride and/or sulfate. L-Lysine is particularly preferred.

The invention provides an isolated polynucleotide from Coryneform bacteria, comprising a polynucleotide sequence which codes for the PtsI protein, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of the phosphotransferase system enzyme I.

The invention also provides the above-mentioned polynucleotide, this preferably being a DNA which is capable of replication, comprising:

(i) the nucleotide sequence shown in SEQ ID No. 1, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide, in particular DNA, which is capable of replication and comprises the nucleotide sequence as shown in SEQ ID No. 1;

a polynucleotide which codes for a polypeptide which comprises the amino acid sequence as shown in SEQ ID No. 2;

a vector containing the polynucleotide according to the invention, in particular a shuttle vector or plasmid vector, and Coryneform bacteria which contain the vector or in which the endogenous ptsI gene is enhanced.

The invention also provides polynucleotides, which substantially comprise a polynucleotide sequence, which are obtainable by screening by means of hybridization of a corresponding gene library of a Coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

Polynucleotides which comprise the sequences according to the invention are suitable as hybridization probes for RNA, cDNA and DNA, in order to isolate, in the full length, nucleic acids or polynucleotides or genes which code for the phosphotransferase system enzyme I, or to isolate those nucleic acids or polynucleotides or genes which have a high similarity of sequence with that of the ptsI gene.

Additionally, methods employing DNA chips, microarrays or similar recombinant DNA technology that enables high throughput screening of DNA and polynucleotides which encode the phosphotransferase system enzyme I protein or polynucleotides with homology to the ptsI gene as described herein. Such methods are known in the art and are described, for example, in Current Protocols in Molecular Biology, Ausebel et al (eds), John Wiley and Sons, Inc. New York (2000).

Polynucleotides which comprise the sequences according to the invention are furthermore suitable as primers with the aid of which DNA of genes which code for the phosphotransferase system enzyme I can be prepared by the polymerase chain reaction (PCR).

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least in particular 70% to 80%, preferably at least 81% to 85%, particularly preferably at least 86% to 90%, and very particularly preferably at least 91%, 93%, 95%, 97% or 99% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of the phosphotransferase system enzyme I, and also those which are at least 70% to 80%, preferably at least 81% to 85%, particularly preferably at least 86% to 90%, and very particularly preferably at least 91%, 93%, 95%, 97% or 99% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using Coryneform bacteria which in particular already produce amino acids and in which the nucleotide sequences which code for the ptsI gene are enhanced, in particular over-expressed.

The term "enhancement" in this connection describes the increase in the intracellular activity of one or more enzymes in a microorganism which are coded by the corresponding DNA, for example by increasing the number of copies of the gene or genes, using a potent promoter or using a gene which codes for a corresponding enzyme having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms which the present invention provides can produce L-amino acids from glucose, sucrose, lactose, fructose, maltose, molasses, starch, cellulose or from glycerol and ethanol. They can be representatives of Coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum* (*C. glutamicum*), are in particular the known wild-type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Corynebacterium melassecola* ATCC17965

*Brevibacterium flavum* ATCC14067

*Brevibacterium lactofermentum* ATCC13869 and

*Brevibacterium divaricatum* ATCC14020 and L-amino acid-producing mutants or strains prepared therefrom.

Preferably, a bacterial strain with enhanced expression of a gap2 gene that encodes a polypeptide with glyceraldehydes 3-phosphate dehydrogenase 2 activity will improve amino acid yield at least 1%.

The new ptsI gene from *C. glutamicum* which codes for the enzyme phosphotransferase system enzyme I (EC 2.7.3.9) has been isolated.

To isolate the ptsI gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the ptsI gene and which, as SEQ ID No. 1, is a constituent of the present invention has been found. The amino acid sequence of the corresponding protein has furthermore been derived from the present DNA sequence by the methods described above. The resulting amino acid sequence of the ptsI gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50° C.–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that Coryneform bacteria produce amino acids in an improved manner after over-expression of the ptsI gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in EP 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in WO 96/15246, in Malumbres et al. (Gene 134, 15–24 (1993)), in JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the ptsI gene according to the invention was over-expressed with the aid of episomal plasmids. Suitable plasmids are those which are replicated in Coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al.,1986, Gene 41: 337–342). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

It has furthermore been found that amino acid exchanges in the section between position 134 to 140 of the amino acid sequence of enzyme I of the phosphotransferase system and/or amino acid exchanges in the section between position 120 and 127 of the amino acid sequence of enzyme I of the phosphotransferase system, shown in SEQ ID No. 2, improve the amino acid production, in particular the lysine production, of Coryneform bacteria.

Preferably, L-lysine at position 123 is exchanged for any other proteinogenic amino acid excluding L-lysine and/or L-arginine at position 137 is exchanged for any other proteinogenic amino acid excluding L-arginine.

At position 123, exchange for L-glutamic acid or L-aspartic acid, in particular L-glutamic acid, is preferred. At position 137, exchange for L-cysteine is preferred.

The base sequence of the allele ptsI-1547 contained in strain DM1547 is shown in SEQ ID No. 3. The ptsI-1547 allele codes for a protein of which the amino acid sequence is shown in SEQ ID No. 4. The protein contains L-glutamic acid at position 123 and L-cysteine at position 137. The DNA sequence of the ptsI-1547 allele (SEQ ID No. 3) contains the base guanine instead of the base adenine contained at position 520 in the ptsI wild-type gene (SEQ ID No. 1) and the base thymine instead of the base cytosine contained at position 562.

Conventional mutagenesis processes using mutagenic substances, such as, for example, N-methyl-N'-nitro-N-nitrosoguanidine or ultraviolet light can be used for the mutagenesis. In vitro methods, such as, for example, a treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger [Genetic Engineering for Beginners], Spektrum Akademischer Verlag, Heidelberg, 1993) or the polymerase chain reaction (PCR) such as is described in the handbook by Newton and Graham (PCR, Spektrum Akademischer Verlag, Heidelberg, 1994), can furthermore be used for the mutagenesis.

The corresponding alleles or mutations are sequenced and introduced into the chromosome by the method of gene replacement such as is described, for example, by Peters-Wendisch et al. (Microbiology 144, 915–927 (1998)) for the pyc gene of *C. glutamicum*, by Schäfer et al. (Gene 145:

69–73 (1994)) for the hom-thrB gene region of *C. glutamicum* or by Schäfer et al. (Journal of Bacteriology 176: 7309–7319 (1994)) for the cg1 gene region of *C. glutamicum*. The corresponding alleles or the associated proteins can optionally be enhanced in turn.

In addition, it may be advantageous for the production of L-amino acids to enhance, in particular over-express one or more enzymes of the particular biosynthesis pathway, of glycolysis, of anaplerosis, of the citric acid cycle, of the pentose phosphate cycle, of amino acid export and optionally regulatory proteins, in addition to the ptsI gene.

Thus, for the preparation of L-amino acids, in addition to enhancement of the ptsI gene, one or more endogenous genes chosen from the group consisting of

- the dapA gene which codes for dihydrodipicolinate synthase (EP-B 0 197 335),
- the gap gene which codes for glyceraldehyde 3-phosphate dehydrogenase (Eikmanns (1992), Journal of Bacteriology 174:6076–6086),
- the tpi gene which codes for triose phosphate isomerase (Eikmanns (1992), Journal of Bacteriology 174:6076–6086),
- the pgk gene which codes for 3-phosphoglycerate kinase (Eikmanns (1992), Journal of Bacteriology 174:6076–6086),
- the zwf gene which codes for glucose 6-phosphate dehydrogenase (JP-A-09224661),
- the pyc gene which codes for pyruvate carboxylase (DE-A-198 31 609),
- the mqo gene which codes for malate-quinone oxidoreductase (Molenaar et al., European Journal of Biochemistry 254, 395–403 (1998)),
- the lysC gene which codes for a feed-back resistant aspartate kinase (Accession No. 26512; EP-B-0387527; EP-A-0699759),
- the lysE gene which codes for lysine export (DE-A-195 48 222),
- the hom gene which codes for homoserine dehydrogenase (EP-A 0131171)
- the ilvA gene which codes for threonine dehydratase (Möckel et al., Journal of Bacteriology (1992) 8065–8072)) or the ilvA(Fbr) allele which codes for a "feed back resistant" threonine dehydratase (Möckel et al., (1994) Molecular Microbiology 13: 833–842),
- the ilvBN gene which codes for acetohydroxy-acid synthase (EP-B 0356739),
- the ilvD gene which codes for dihydroxy-acid dehydratase (Sahm and Eggeling (1999) Applied and Environmental Microbiology 65: 1973–1979),
- the zwa1 gene which codes for the Zwa1 protein (DE: 19959328.0, DSM 13115)

can be enhanced, in particular over-expressed.

It may furthermore be advantageous for the production of L-amino acids, in addition to the enhancement of the ptsI gene, for one or more genes chosen from the group consisting of:

- the pck gene which codes for phosphoenol pyruvate carboxykinase (DE 199 50 409.1; DSM 13047),
- the pgi gene which codes for glucose 6-phosphate isomerase (U.S. Ser. No. 09/396,478; DSM 12969),
- the poxB gene which codes for pyruvate oxidase (DE: 1995 1975.7; DSM 13114),
- the zwa2 gene which codes for the Zwa2 protein (DE: 19959327.2, DSM 13113)

to be attenuated, in particular reduced in expression.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

In addition to over-expression of the ptsI gene it may furthermore be advantageous for the production of amino acids to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e. g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by ion exchange chromatography with subsequent ninhydrin derivation, or it can be carried out by reversed phase HPLC, for example as described by Lindroth et al. (Analytical Chemistry (1979) 51: 1167–1174).

A pure culture of the *Corynebacterium glutamicum* strain DM1547 was deposited on Jan. 16, 2001 at the Deutsche Sammlung für Mikroorganismen und Zellkylturen (DSMZ=German Collection of Microorganisms and Cell Cultures, Braunschweig, Germany) as DSM 13994 in accordance with the Budapest Treaty.

A pure culture of the *Escherichia coli* strain DH5alphamcr/pEC-K18mob2ptsIexp (=DH5αmcr/pEC-K18mob2ptsIexp) was deposited on May 2, 2001 at the Deutsche Sammlung für Mikroorganismen und Zellkylturen (DSMZ=German Collection of Microorganisms and Cell Cultures, Braunschweig, Germany) as DSM 14278 in accordance with the Budapest Treaty.

The process according to the invention is used for fermentative preparation of amino acids.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA).

Methods for transformation of *Escherichia coli* are also described in this handbook.

The composition of the usual nutrient media, such as LB or TY medium, can also be found in the handbook by Sambrook et al.

Having generally described this invention, a further understanding can be obtained by reference to certain specific examples which are provided herein for purposes of illustration only, and are not intended to be limiting unless otherwise specified.

EXAMPLES

Example 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

Example 2

Isolation and Sequencing of the ptsI Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed an open reading frame of 1707 base pairs, which was called the ptsI gene. The ptsI gene codes for a protein of 568 amino acids.

The DNA section lying upstream of SEQ ID No. 1 was identified in the same way, this section being shown in SEQ ID No. 5. The ptsI gene region extended by SEQ ID No. 5 is shown in SEQ ID No. 6.

Example 3

Preparation of a Shuttle Vector pEC-K18mob2ptsIexp for Enhancement of the ptsI Gene in *C. glutamicum*

3.1 Cloning of the ptsI gene in the vector pCR®BLUNT II

From the strain ATCC 13032, chromosomal DNA was isolated by the method of Eikmanns et al. (Microbiology 140: 1817–1828 (1994)). On the basis of the sequence of the ptsI gene known for *C. glutamicum* from example 2, the following oligonucleotides were chosen for the polymerase chain reaction (see also SEQ ID No. 8 and SEQ ID No. 9):

```
ptsI2exp1:
5'-GGC TGA CCA TGC TTA ACC TC-3'      (SEQ ID NO:8)

ptsI2exp2:
5'AGA CTG CTG CGT CGA TCA CT-3'       (SEQ ID NO:9)
```

The primers shown were synthesized by ARK Scientific GmbH Biosystems (Darmstadt, Germany) and the PCR reaction was carried out by the standard PCR method of Innis et al. (PCR Protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment approx. 2121 bp in size, which carries the ptsI gene with the potential promoter region. The DNA sequence of the amplified DNA fragment was checked by sequencing.

The amplified DNA fragment was ligated with the ZERO BLUNT™ Kit of Invitrogen Corporation (Carlsbad, Calif., USA: Catalogue Number K2700-20) in the vector pCR®BLUNT II (Bernard et al., Journal of Molecular Biology, 234: 534–541 (1993)).

The *E. coli* strain TOP10 was then electroporated with the ligation batch (Hanahan, In: DNA cloning. A Practical Approach. Vol. I, IRL-Press, Oxford, Washington D.C., USA, 1985). Selection for plasmid-carrying cells was made by plating out the transformation batch on LB agar (Sambrook et al., Molecular Cloning: A Laboratory Manual. $2^{nd}$ Ed, Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCRB1-ptsIexp.

3.2 Preparation of the *E. coli–C. glutamicum* Shuttle Vector pEC-K18mob2

The *E. coli–C. glutamicum* shuttle vector was constructed according to the prior art. The vector contains the replication region rep of the plasmid pGA1 including the replication effector per (U.S. Pat. No. 5,175,108; Nesvera et al., Journal of Bacteriology 179, 1525–1532 (1997)), the kanamycin resistance-imparting aph(3')-IIa gene of the transposon Tn5 (Beck et al., Gene 19, 327–336 (1982)), the replication region oriV of the plasmid pMB1 (Sutcliffe, Cold Spring Harbor Symposium on Quantitative Biology 43, 77–90 (1979)), the lacZα gene fragment including the lac promoter and a multiple cloning site (mcs) (Norrander, J. M. et al., Gene 26, 101–106 (1983)) and the mob region of the plasmid RP4 (Simon et al., Bio/Technology 1:784–791 (1983)).

The vector pEC-K18mob2 constructed was transferred into *C. glutamicum* DSM5715 by means of electroporation (Liebl et al., 1989, FEMS Microbiology Letters, 53:299–303). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927), cleaved with the restriction endonucleases EcoRI and HindIII, and the plasmid was checked by subsequent agarose gel electrophoresis.

The plasmid construction thus obtained was called pEC-K18mob2 and is shown in FIG. 1. The strain obtained by electroporation of the plasmid pEC-K18mob2 in the *C. glutamicum* strain DSM5715 was called DSM5715/pEC-K18mob2 and deposited on Jan. 20, 2000 as DSM 13245 at the Deutsche Sammlung für Mikroorganismen und Zellkylturen (DSMZ=German Collection of Microorganisms and Cell Cultures, Braunschweig, Germany) in accordance with the Budapest Treaty.

3.3 Cloning of ptsI in the *E. coli–C. glutamicum* Shuttle Vector pEC-K18mob2

For cloning of the ptsI gene in the *E. coli–C. glutamicum* shuttle vector pEC-K18mob2 described in example 3.2, plasmid DNA of pEC-K18mob2 was cleaved completely with the restriction endonuclease EcoRI and treated with alkaline phosphatase (Alkaline Phosphatase, Roche Diagnostics GmbH, Mannheim, Germany).

The vector pCRB1-ptsIexp was isolated from *Escherichia coli* Top10 and cleaved completely with the restriction endonuclease EcoRI and the fragment approx. 2140 bp in size with the ptsI gene was purified from a 0.8% agarose gel (QIAquick Gel Extraction Kit der Firma Qiagen, Hilden, Germany). The fragment with the ptsI gene was then ligated with the vector pEC-K18mob2 (T4-Ligase, Roche Diagnostics GmbH, Mannheim; Germany). The ligation batch was transformed in the *E. coli* strain DH5αmcr (Hanahan, Ind.: DNA cloning. A Practical Approach. Vol. I, IRL-Press, Oxford, Washington D.C., USA). Selection for plasmid-carrying cells was made by plating out the transformation batch on LB agar (Sambrook et al., Molecular Cloning: A Laboratory Manual. $2^{nd}$ Ed., Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen (Hilden, Germany) and checked by treatment with the restriction enzyme PstI with subsequent agarose gel electrophoresis. The plasmid was called pEC-K18mob2ptsIexp and is shown in FIG. 2.

The abbreviations and designations used have the following meaning:

| | |
|---|---|
| Kan: | Resistance gene for kanamycin |
| per: | Gene for control of the number of copies from pGA1 |
| oriV: | Co1E1-similar origin from pMB1 |
| rep: | Plasmid-coded replication region from *C. glutamicum* plasmid pGA1 |
| RP4mob: | RP4 mobilization site |

-continued

| | |
|---|---|
| ptsI: | ptsI gene from *C. glutamicum* |
| EcoRI: | Cleavage site of the restriction enzyme EcoRI |
| HindIII: | Cleavage site of the restriction enzyme HindIII |
| PstI: | Cleavage site of the restriction enzyme PstI |

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide, which encodes a polypeptide having the amino acid sequence of SEQ ID NO: 2 or which encodes a polypeptide that is a fragment of SEQ ID NO: 2 and that has phosphotransferase system I enzyme activity.

2. The isolated polynucleotide of claim 1 that comprises SEQ ID NO: 1 or SEQ ID NO: 6.

3. An isolated polynucleotide, which encodes a polypeptide having phosphotransferase system enzyme I activity, and which is (a) at least 90% identical to the polynucleotide of SEQ ID NO: 1 or SEQ ID NO: 6, or (b) hybridizes under stringent conditions to the polynucleotide of SEQ ID NO: 1 or SEQ ID NO: 6 or the full complement of SEQ ID NO: 1 or SEQ ID NO: 6, wherein stringent conditions comprise washing in 5×SSC at a temperature of 68° C.

4. An isolated polynucleotide that is fully complementary to the isolated polynucleotide of claim 3.

5. The isolated polynucleotide of claim 3 that is at least 95% identical to the polynucleotide of SEQ ID NO: 1 or SEQ ID NO: 6.

6. The isolated polynucleotide of claim 3 that is at least 99% identical to the polynucleotide of SEQ ID NO: 1 or SEQ ID NO: 6.

7. An isolated polynucleotide that encodes a polypeptide having phosphotransferase system enzyme I activity that is at least 90% identical to SEQ ID NO: 2.

8. The isolated polynucleotide of claim 3, which hybridizes under stringent conditions to the polynucleotide of SEQ ID NO: 1 or SEQ ID NO: 6 or the full complement of SEQ ID NO: 1 or SEQ ID NO: 6.

9. The isolated polynucleotide of claim 3, which encodes a protein having phosphotransferase system enzyme I activity that has at least one amino acid exchange in the section between amino acid residues 120 and 127 and at least one amino acid exchange in the section between residues 134 and 140 of SEQ ID NO: 2; or that has at least one amino acid exchange in the section between residues 134 and 140 of SEQ ID NO: 2.

10. A probe or primer, which consists of a fragment of at least 15 consecutive nucleotides of SEQ ID NO: 1 or SEQ ID NO: 6 or at least 15 consecutive nucleotides of the full complement of SEQ ID NO: 1 or SEQ ID NO: 6.

11. A vector comprising the isolated polynucleotide of claim 1.

12. A vector comprising the isolated polynucleotide of claim 3.

13. A host cell comprising the isolated polynucleotide of claim 1.

14. A host cell comprising the isolated polynucleotide of claim 3.

15. The host cell of claim 13, which is a coryneform bacterium.

16. The host cell of claim 14, which is a coryneform bacterium.

17. The host cell of claim 13, which is selected from the group consisting of *Corynebacterium glutamicum, Corynebacterium acetoglutamicum, Corynebacterium acetoacidophilum, Corynebacterium thermoaminogenes, Corynebacterium melassecola, Brevibacterium flavum, Brevibacterium lactofermentum,* and *Brevibacterium divaricatum.*

18. The host cell of claim 14, which is selected from the group consisting of *Corynebacterium glutamicum, Corynebacterium acetoglutamicum, Corynebacterium acetoacidophilum, Corynebacterium thermoaminogenes, Corynebacterium melassecola, Brevibacterium flavum, Brevibacterium lactofermentum,* and *Brevibacterium divaricatum.*

19. A biologically pure culture of a coryneform bacterium that comprises multiple copies of the polynucleotide of claim 3, or that comprises the polynucleotide of claim 3 in combination with an exogenous promoter, regulatory region, ribosome binding site or expression cassette.

20. The coryneform bacterium of claim 19 that comprises multiple copies of the polynucleotide of SEQ ID NO: 1.

21. The coryneform bacterium of claim 19 that comprises multiple copies of the polynucleotide of SEQ ID NO: 3.

22. The coryneform bacterium of claim 19 that comprises multiple copies of the polynucleotide of SEQ ID NO: 6.

23. A biologically pure culture of *Corynebacterium glutamicum* DSM 13994.

24. *Escherichia coli* DSM 14278.

25. A process for screening for a polynucleotide, which encodes a protein having phosphotransferase system I activity comprising:

a. hybridizing the isolated polynucleotide of claim 1 or its complement to the polynucleotide to be screened;

b. expressing the screened polynucleotide to produce a protein; and c. detecting the presence or absence of phosphotransferase system enzyme I activity in said protein.

26. A process for screening for a polynucleotide, which encodes a protein having phosphotransferase system I activity comprising:

a. hybridizing the isolated polynucleotide of claim 3 or its complement to the polynucleotide to be screened;

b. expressing the screened polynucleotide to produce a protein; and c. detecting the presence or absence of phosphotransferase system enzyme I activity in said protein.

27. A method for detecting a nucleic acid with at least 70% homology to the polynucleotide of SEQ ID NO: 1 or SEQ ID NO: 6 comprising:

contacting a nucleic acid sample with the probe or primer of claim 10.

28. A method of detecting a nucleic acid with at least 80% homology to the polynucleotide of SEQ ID NO: 1 or SEQ ID NO: 6, comprising:

contacting a nucleic acid sample with the primer of claim 10.

29. A method for screening for a polynucleotide which encodes a protein having phosphotransferase system enzyme I activity comprising:

a. hybridizing the isolated polynucleotide of SEQ ID NO: 1 or SEQ ID NO: 6 or its full complement to the polynucleotide to be screened;

b. expressing the screened polynucleotide to produce a protein; and c. detecting the presence or absence of phosphotransferase system enzyme I activity.

30. A method for making a phosphotransferase system enzyme I protein, comprising a. culturing the host cell of claim 13 for a time and under conditions suitable for expression of the phosphotransferase system enzyme I protein; and b. collecting the phosphotransferase system enzyme I protein.

31. A method for making a phosphotransferase system enzyme I protein, comprising a. culturing the host cell of claim 14 for a time and under conditions suitable for expression of the phosphotransferase system enzyme I protein; and b. collecting the phosphotransferase system enzyme I protein.

32. The polynucleotide of claim 3 that comprises SEQ ID NO: 1.

33. The polynucleotide of claim 3 that comprises SEQ ID NO: 6.

34. The polynucleotide of claim 3 that comprises SEQ ID NO: 3.

35. An isolated coryneform bacterium comprising a polynucleotide encoding a protein having phosphotransferase system enzyme I activity and having the amino acid sequence of SEQ ID NO: 4.

36. The isolated coryneform bacterium of claim 35 comprising a polynucleotide, wherein said polynucleotide is SEQ ID NO: 3.

* * * * *